(12) United States Patent
Parry et al.

(10) Patent No.: US 10,875,830 B2
(45) Date of Patent: Dec. 29, 2020

(54) METHOD OF TREATMENT

(71) Applicant: Conopco, Inc., Englewood Cliffs, NJ (US)

(72) Inventors: Neil James Parry, Tarporley (GB); Paolo Pantalone, Nottingham (GB); Paul Williams, Nottingham (GB)

(73) Assignee: Conopeo, Inc., Englewood Cliffs, NJ (US)

( * ) Notice: Subject to any disclaimer, the term of this patent is extended or adjusted under 35 U.S.C. 154(b) by 0 days.

(21) Appl. No.: 16/317,269

(22) PCT Filed: Jul. 13, 2017

(86) PCT No.: PCT/EP2017/067782
§ 371 (c)(1),
(2) Date: Jan. 11, 2019

(87) PCT Pub. No.: WO2018/015279
PCT Pub. Date: Jan. 25, 2018

(65) Prior Publication Data
US 2019/0300479 A1    Oct. 3, 2019

(30) Foreign Application Priority Data

Jul. 21, 2016   (EP) .................................. 16180612

(51) Int. Cl.
| | | |
|---|---|---|
| *A61K 31/40* | (2006.01) |
| *A61K 31/4015* | (2006.01) |
| *C07D 207/44* | (2006.01) |
| *A61P 31/04* | (2006.01) |
| *A61P 11/00* | (2006.01) |
| *A61K 9/00* | (2006.01) |
| *A61K 31/402* | (2006.01) |
| *C07D 207/333* | (2006.01) |

(52) U.S. Cl.
CPC .......... *C07D 207/44* (2013.01); *A61K 9/0073* (2013.01); *A61K 31/40* (2013.01); *A61K 31/402* (2013.01); *A61K 31/4015* (2013.01); *A61P 11/00* (2018.01); *A61P 31/04* (2018.01); *C07D 207/333* (2013.01)

(58) Field of Classification Search
CPC ........................... A61K 31/40; A61K 31/4015
USPC ....................................................... 514/424
See application file for complete search history.

(56) References Cited

U.S. PATENT DOCUMENTS

| | | |
|---|---|---|
| 3,905,965 A | 9/1975 | Martel et al. |
| 5,474,995 A | 12/1995 | Ducharme et al. |
| 5,637,579 A | 6/1997 | Hubschwerlen et al. |

(Continued)

FOREIGN PATENT DOCUMENTS

| | | |
|---|---|---|
| FR | 2059965 | 6/1971 |
| WO | WO2004016588 | 2/2004 |

(Continued)

OTHER PUBLICATIONS

IPRP1 in PCTEP2016061703; dated Jan. 25, 2018.
(Continued)

*Primary Examiner* — Craig D Ricci
*Assistant Examiner* — Janet L. Coppins
(74) *Attorney, Agent, or Firm* — Greenberg Traurig, LLP (57) ABSTRACT

Lactams for use in the treatment of respiratory tract infections, including chronic lung infections in patients having cystic fibrosis.

1 Claim, 6 Drawing Sheets

(56) References Cited

U.S. PATENT DOCUMENTS

| 2002/0032230 | A1 | 3/2002 | Pal et al. |
| 2006/0194865 | A1 | 8/2006 | Araldi et al. |
| 2010/0035948 | A1 | 2/2010 | Kumar et al. |
| 2010/0286227 | A1 | 11/2010 | Sheu et al. |
| 2011/0152243 | A1 | 6/2011 | Wishart et al. |
| 2015/0351393 | A1 | 12/2015 | Parry et al. |

FOREIGN PATENT DOCUMENTS

| WO | WO2007085042 | | 8/2007 | |
| WO | WO-2007085042 A1 * | | 8/2007 | ........... C07D 207/36 |
| WO | WO2014118240 | | 8/2014 | |
| WO | WO2014183164 | | 11/2014 | |
| WO | WO2018015278 | | 1/2018 | |
| WO | WO2018015279 | | 1/2018 | |
| WO | WO2018015280 | | 1/2018 | |

OTHER PUBLICATIONS

Search Report and Written Opinion in PCTEP2017067782; dated Aug. 30, 2017.
Search Report and Written Opinion in EP16180612; dated Jan. 18, 2017.
Search Report and Written Opinion in EP16180598; dated Jan. 18, 2017.
Search Report and Written Opinion in PCTEP2017067781; dated Aug. 30, 2017
Search Report and Written Opinion in PCTEP2017067783; dated Oct. 20, 2017.
Ondrej Krenk et al.; Methodology for Synthesis of Enantiopure 3,5-Disubstituted Pyrrol-2-ones; European Journal of Organic Chemistry; 2015; pp. 5414-5423; XP002752111.
Search Report and Written Opinion in EP16180590; dated Jan. 18, 2017.
Goldufsky et al.; Pseudomonas aeruginosa uses T3SS to inhibit diabetic found healing; Wound Repair Regen.; 2015; pp. 557-564; 23(4).

* cited by examiner

METHOD OF TREATMENT

This application is a national phase filing under 35 USC 371 of International Application No. PCT/EP2017/067782, filed on Jul. 13, 2017, which claims priority from EP16180612.0 filed Jul. 21, 2016, the contents of which are incorporated herein in their entirety for all purposes.

FIELD OF THE INVENTION

The invention relates to lactams for use in a method of treatment of respiratory tract infections.

BACKGROUND

Despite advances in antibiotics, bacterial respiratory tract infections still present a major problem, especially in the very young, the elderly, and those suffering from certain disorders that compromise the pulmonary and/or immune systems. Chronic respiratory tract infections reduce quality of life for suffers, place a significant burden on healthcare systems, and often shorten life.

For example, cystic fibrosis patients usually suffer chronic bacterial lung infections. The average life expectancy for a person having cystic fibrosis in the developed world is less than 50 years, and 80% of these deaths are attributed to lung problems. Indeed, the most consistent aspect of clinical therapy in cystic fibrosis is limiting and treating the lung damage caused by thick mucus and infection, with the goal of maintaining quality of life. Intravenous, inhaled, and oral antibiotics are used to treat chronic and acute infections.

Owing to the chronic nature of many of these bacterial infections, long term treatment with antibiotics is often required. Similarly, owing to the danger of virulent respiratory conditions, it is common for suffers of conditions such as cystic fibrosis to be treated prophylactically. This long term use of antimicrobial agents can result in bacterial evolution to develop resistance, both within the local environment of a particular patient's respiratory system and the patient population at large.

The emergence of drug-resistant bacteria and fungi presents a significant medical and public health problem. Consequently, there is an urgent need for the development of antimicrobial agents that can overcome drug resistance problems. Bacteria and fungi generally develop drug resistance in four ways: producing metabolizing enzymes for the degradation of the drugs, modifying their targets to render the drugs ineffective, expressing a high level of efflux proteins that "pump" the drug out in order to lower its concentration, and inducing biofilm formation to prevent permeation of drugs into the bacteria.

WO2007/085042 (Biosignal Limited) describes certain lactam structures and their use in the treatment of bacterial infections.

WO2014/118240 (Unilever) describes antimicrobial compositions comprising a lactam and a hydrotrope.

WO2014/183164 (Kumar, Perry and Kit) describes certain N-functionalised dihydropyrrolone compounds and methods for preparing surfaces to which the dihydropyrrolone compounds are attached.

SUMMARY OF THE INVENTION

The invention is based on the inventors' understanding and insight into the unusual biological properties of certain lactam compounds, and the utility of these compounds in methods of treatment owing to their biological profile.

The lactams described herein are antibacterial. Their particular biological profile makes them surprisingly suitable for the treatment of respiratory tract infections, in particular in the long term treatment (including prophylactic treatment) of chronic respiratory tract infections.

In a first aspect, the invention therefore relates to a lactam for use in a method of treatment of a respiratory tract infection in a subject.

Suitably, the infection is a bacterial infection in which *Pseudomonas*, (usually but not necessarily *P. aeruginosa*) is implicated.

Suitably, the lactam is a lactam of Formula I or Formula II:

wherein Ar is an optionally substituted phenyl group and $R^1$ is H or $C_{1-4}$alkyl.

Accordingly, in a first aspect, the invention may provide a lactam of Formula I or Formula II, for use in a method of treatment of a respiratory tract infection in a subject, wherein Ar is optionally substituted phenyl, said optional substituents being selected from halogen and $C_{1-4}$alkyl.

In some cases, Ar is unsubstituted. In some cases, Ar is substituted. In this case, each of the 2, 3, 4, 5, and 6 positions may be substituted or unsubstituted. For example, Ar may be 2,4-disubstituted, 3,4-disubstituted, 2,4,6-trisubstituted, 3,4,5-trisubstituted, 2,3,4-trisubstituted, 2,4,5-trisubstituted, etc.

Suitable substituents $R^2$ include halogen, $C_{1-4}$alkyl, OH, $C_{1-4}$alkoxy, $CF_3$, $OF_3$.

In some cases, Ar has a substituent at the 4-position. In some cases, the substituent at the 4-position is chloro, fluoro or methyl, optionally chloro or methyl.

For example, Ar may be where n is 0, 1, 2, 3, or 4, preferable 0 or 1, most preferably 0.

Preferably, the lactam is a lactam of Formula Ia or Formula IIa:

Ia

IIa wherein $R^1$ is H or $C_{1-4}$alkyl (preferably methyl);

$R^2$ is selected from H, halogen, $C_{1-4}$alkyl, OH, $C_{1-4}$alkoxy, $CF_3$, $OF_3$.

In some cases, the lactam is a lactam of formula Ia. In some cases, the lactam is a lactam of formula IIa.

Preferably, $R^1$ is H.

Preferably, $R^2$ is halogen (preferably, F, Cl, or Br), or $C_{1-4}$alkyl (preferably methyl).

Preferably, $R^2$ is halogen. Halogen includes F, Cl, Br, and I. For example, $R^2$ may be fluoro or choro, for example chloro.

Preferred lactams may include:

4-(4-chlorophenyl)-5-methylene-pyrrol-2-one (Ref. 488)

5-methylene-4-(p-tolyl)pyrrol-2-one (Ref. 491)

-continued

4-(4-fluorophenyl)-5-methylene-pyrrol-2-one (Ref. 310)

4-phenyl-5-hydroxy-5-methyl-1H-pyrrol-2-one (Ref. 131)

4-(4-fluorophenyl)-5-hydroxy-5-methyl-1H-pyrrol-2-one (Ref. 258)

4-(4-bromophenyl)-5-hydroxy-5-methyl-1H-pyrrol-2-one (Ref. 316)

4-phenyl-5-methylene-pyrrol-2-one 4-(4-bromophenyl)-5-methylene-pyrrol-2-one

4-(2-fluorophenyl)-5-methylene-pyrrol-2-one 4-(4-chlorophenyl)-5-hydroxy-5-methyl-1H-pyrrol-2-one 4-(2-chlorophenyl)-5-hydroxy-5-methyl-1H-pyrrol-2-one 4-(2-chlorophenyl)-5-methylene-pyrrol-2-one 4-(3-chlorophenyl)-5-methylene-pyrrol-2-one 4-(3-chlorophenyl)-5-hydroxy-5-methyl-1H-pyrrol-2-one 4-(4-chlorophenyl)-1-methyl-5-methylene-pyrrol-2-one 4-(4-hydroxy-3-methoxy-phenyl)-5-methylene-pyrrol-2-one Especially preferred lactams include: 4-(4-chlorophenyl)-5-methylene-pyrrol-2-one (Ref. 488); 5-methylene-4-(p-tolyl)pyrrol-2-one (Ref. 491); and 4-(4-fluorophenyl)-5-methylene-pyrrol-2-one (Ref. 310).

The lactams may be useful for the treatment of a variety of respiratory tract infections in a subject, but may be especially useful for the treatment of bacterial lower respiratory tract infections such as lung infections. The bacterial infection may result in an acute or chronic lung infection, or may cause a recurring lung infection and thus treatment is of an acute, chronic and/or recurring lung infection.

The lactams of Formula I and II act to prevent the formation of, retard or prevent the growth and development of, and/or reduce the extent of a bacterial biofilm. The present invention thus includes lactams of Formula I and II for use in the treatment of a bacterial infection in a subject by preventing the formation of, retarding or preventing the growth and development of, and/or reducing the extent of a bacterial biofilm. *Pseudomonas*, typically *P. aeruginosa*, may be implicated in the bacterial biofilm.

In the present invention, the subject being treated is preferably a mammalian subject and most preferably a human.

While the lactams may be used for treatment in a variety of subjects having respiratory tract infections, an advantage of the methods described herein is the unusual biological profile of the lactams, which may make the lactams especially suitable for the treatment of cystic fibrosis patients. Accordingly, in some cases, the subject is diagnosed as having cystic fibrosis.

In some subjects, and particularly in subjects diagnosed as having cystic fibrosis, the lactams may be used prophylactically for preventing the occurrence or recurrence of a respiratory tract infection.

The lactams of Formula I and II may be used as the first line of treatment of a respiratory tract infection, or may be used in subjects already treated with other antibiotics for the same infection, for example those who have not shown a satisfactory response to those other antibiotics.

If appropriate, the lactams of Formula I and II may be administered together with other treatments, including other antibiotic treatments.

In a second aspect, the invention provides a method of treatment of a respiratory tract infection, the method comprising administering to a subject a therapeutically effective amount of a lactam of Formula I or Formula II.

In a third aspect, the invention provides the use of a lactam of Formula I or Formula II in the manufacture of a medicament for the treat of respiratory tract infections.

In a fourth aspect, the invention provides a pharmaceutical composition comprising a lactam of Formula I or Formula II, wherein the composition is formulated for parenteral administration.

In a fifth aspect, the invention provides a pharmaceutical composition comprising a lactam of Formula I or Formula II, wherein the composition is formulated for administration by insufflation and/or inhalation.

It will be appreciated that all preferences described with respect to the first aspect apply similarly to the second, third, fourth and fifth aspects, as appropriate.

DETAILED DESCRIPTION

The invention will now be described with reference to the following drawings in which:
LB medium=Lysogeny broth ex. Sigma Aldrich UK.
Lactam 131=4-phenyl-5-hydroxy-5-methyl-1H-pyrrol-2-one
Lactam 258=4-(4-fluorophenyl)-5-hydroxy-5-methyl-1H-pyrrol-2-one
Lactam 310=4-(4-fluorophenyl)-5-methylene-pyrrol-2-one
Lactam 316=4-(4-bromophenyl)-5-hydroxy-5-methyl-1H-pyrrol-2-one
Lactam 488=4-(4-chlorophenyl)-5-methylene-pyrrol-2-one
Lactam 491=5-methylene-4-(p-tolyl)pyrrol-2-one

PSEUDOMONAS AERUGINOSA

*Pseudomonas aeruginosa* is a pathogen important in certain respiratory tract disorders and is associated with severe and often chronic infections in cystic fibrosis (CF) patients. There are a number of *P. aeruginosa* strains, including PA01, PA7, USBPP-PA14 and strain 2192. Except where indicated otherwise, a reference to *P. aeruginosa* is intended to refer to any and all strains.

The methods described herein may be directed to treatment of respiratory tract infections in which *P. aeruginosa* is implicated. The *P. aeruginosa* may be a strain that produces AQs (alkylquinoline compounds). The *P. aeruginosa* may be a strain that produces one or both of PQS (*Pseudomonas* quinolone signal; 2-heptyl-3-hydroxy-4-(1H)-quinolone) and HHQ (4-hydroxy-2-heptylquinoline). The *P. aeruginosa* may be a strain belonging to one of the two major *P. aeruginosa* genomic groups (PAO1 and PA14).

Cystic Fibrosis

The methods described herein may be especially suitable for patients having cystic fibrosis. Accordingly, the method may be a method of treating a subject who has been diagnosed with cystic fibrosis. Cystic fibrosis is a genetic disorder inherited in an autosomal recessive manner. Sufferers have mutations in both copies of the CTFR gene (for the cystic fibrosis transmembrane conductance regulator (CFTR) protein) meaning that CFTR is not functional. The most common mutation is ΔF508.

As used herein, the terms cystic fibrosis sufferer and cystic fibrosis patient refer to a subject who has been medically diagnosed with cystic fibrosis and/or has mutations in copies of the CTFR gene.

Quorum Sensing

Quorum sensing (QS) is a mechanism whereby microorganisms, and in particular bacteria, communicate with each other and exhibit community-wide behaviour coordination through the secretion and detection of chemical signals called autoinducers (AIs). Quorum sensing has been demonstrated in a large number of bacteria species/strains and important in regulating bacterial virulence, drug resistance, expression of efflux transporters, and biofilm formation, and therefore is attracting attention in the antimicrobial field. (*Frontiers in microbiology* 6 (1036) September 2015).

Quorum sensing is a cell-density based intercellular communication system to regulate collective behaviour, which plays a key role in regulation of bacterial virulence and biofilm formation. The process relies on the production, release and group-wide detection of signal molecules called autoinducing peptides (AIPs), which in gram-negative bacteria are typically homoserine lactones, (HSLs), especially N-acyl-homoserine lactones (AHLs). Other quorum sensing molecules are known, including epinephrine/norepinephrine.

Biofilm formation enables the bacteria to resist antibiotics because once the bacteria sense that the outer layer of the biofilm is being destroyed, the inner layers will grow stronger to re-establish the community. The present invention is based on the inventors' investigation into the properties of certain lactams as described herein and their insight into the way in which said lactams influence QS in gram negative bacteria such as *P. aeruginosa*.

The QS network of *P. aeruginosa* is organised in a multi-layered hierarchy consisting of at least four interconnected signalling mechanisms and demonstrates plasticity, in that it can respond to bacterial population changes and possibly also environmental stress cues. *P. aeruginosa* orchestrates biofilm formation—and production of virulence factors—by reliance on two QS systems, both part of the LuxI/R signalling cascade, the Las and Rhl systems.

In *Pseudomonas aeruginosa*, the acyl-homoserine lactone (AHL) and alkyl quinolone (AQ) QS systems are important for virulence and biofilm formation. One acyl-HSL QS regulator is LasR. A non-AHL signalling molecule produced by *P. aeruginosa* is known as PQS (*Pseudomonas* quinolone signal), which is 2-heptyl-3-hydroxy-4-(1H)-quinolone.

Biofilm

The term "biofilm" as used herein refers to biological films that develop and persist at interfaces in aqueous environments, particularly in this case as foci of chronic infections and on medical implants used in the respiratory system. These biological films are composed of microorganisms embedded in organic gelatinous matrices composed of one or more matrix polymers that are secreted by the resident microorganisms. Biofilms can develop into macroscopic structures and are also capable of trapping nutrients and particulates that can contribute to their enhanced development and stability. Biofilms can also prevent penetration of antimicrobial agents, which may lead to persistent infections. Formation of biofilms provides bacteria with a protected environment such as within the lungs with can withstand various stresses, including many antibiotic treatments.

Pharmaceutical Compositions

The invention further provides pharmaceutical compositions comprising a lactam as described herein. It will be appreciated that the pharmaceutical composition will be formulated to be suitable for the intended route of administration. A pharmaceutical composition comprising a lactam of Formula I or II will typically include a pharmaceutically acceptable carrier and may optionally include other therapeutic ingredients.

Typically, compositions as described herein may be ingested, inhaled or administered parenterally (via injection or infusion), although other administration routes including buccal, endosinusial, endotracheal, intrabronchial, and transtracheal are also envisaged. The compound may be administered locally or systemically.

In some cases, the composition is formulated for oral administration and may be provided as a tablet, capsule, liquid or similar. In some cases, the composition is formulated for parenteral administration and may be presented in unit- or multi-dose containers such as sealed ampoules or vials, and/or may be stored in a lyophilized condition. In some cases, the composition is formulated for administration by insufflation and/or inhalation. For example, the composition may be provided via an inhaler or nebuliser, suitably a metered-dose inhaler or nebuliser. Accordingly, the composition may be formulated for administration as an aerosol, either a fine solid (for example micronized) particles or liquid droplets. A liquefied propellant may be used when the composition is presented as a suspension or solution formulation.

Preferably the composition is formulated to provide an effective amount of the lactam. The term "effective amount" as used herein refers to an amount of the lactam at least sufficient to achieve a desired modulation of the activity or physiological property of a microbial population. The effective amount is determined, at least in part, upon the compound used, the microbial species present, the structure, system, or host, and the desired level of regulation. Modulating the activity or physiological property of the microbial population includes, but is not limited to, slowing, attenuating or inhibiting the growth of a microbial population and/or the colonization of a surface; causing a partial or total reduction in a microbial population; inhibiting the formation, development or growth of a biofilm, and partially or totally reducing the extent of a biofilm, and the like.

For administration to human patients, it is expected that the daily dosage level of the lactams will be from 0.01 to 50 mg/kg, for example around 1 mg/kg. The physician in any event will determine the actual dosage most suitable for an individual patient, which will vary with the age, weight and response of the patient. The dose may be administered once, twice or three times per day, as appropriate.

Methods of Treatment

It will be appreciated that the term "methods of treatment" as used herein includes prophylaxis, treatment that hamper bacterial colony population growth, treatments that keep a bacterial colony population stable, and treatments that reduce or eradicate a bacterial population.

The invention relates to methods of treatment for respiratory tract infections, in particular lower respiratory tract infections. These are commonly referred to as lung infections. The lactams described herein may be especially suitable for the treatment of chronic respiratory tract infections. These may also be referred to as lung disease. A chronic condition is characterised by long duration or frequent recurrence.

Chronic bacterial respiratory tract infections present a particular problem in cystic fibrosis (CF) sufferers. Accordingly, the present invention is envisaged for the treatment of bacterial respiratory tract infections in patients that have been diagnosed with cystic fibrosis.

The lungs of individuals with CF are colonized and infected by bacteria from an early age. In the initial stages, common bacteria such as *Staphylococcus aureus* and *Haemophilus influenzae* typically colonize and infect the lungs. Eventually, *P. aeruginosa* (and sometimes *Burkholderia cepacia*) dominates. By 18 years of age, it is estimated 80% of patients with classic CF harbor *P. aeruginosa*, and 3.5% harbor *B. cepacia*.

These bacteria thrive in the altered mucus that is a symptom of CF, which collects in the small airways of the lungs, and adapt to the environment. *P. aeruginosa* in particular is known to form large colonies, known as "mucoid" *P. aeruginosa*, which are rarely seen in people that do not have CF. This includes biofilm formation. Over time, and with prolonged treatment, these colonies develop resistance to commonly used antibiotics, meaning that treatment regimens may need to be frequently altered. This problem is exacerbated as many people with CF are taking one or more antibiotics at all times (even when "healthy" to prophylactically suppress infection).

Owing to their unusual biological profile, the lactams of Formula I and II may be useful in the long term treatment of respiratory tract infections associated with cystic fibrosis. This is because, owing to their selective interactions with the various bio-pathways of the bacteria, and in particular *P. aeruginosa*, the lactams may permit population control and reduction without triggering the mechanisms that are thought to lead to evolutionary resistance.

In some cases, the bacterial infection is an infection in which *Pseudomonas*, (usually but not necessarily *P. aeruginosa*) is implicated.

The methods described herein may be suitable for long term use. Accordingly, the methods may include regular administration of the lactam to a subject for a period of at least several weeks, several months, at least one year, at least two years, at least three years, at least 5 years, at least 8 years, or at least 10 years.

EXAMPLES

To elucidate the mechanism of action of compounds described herein, the impact of each lactam on both N-acyl-homoserine lactone (AHL) and 2-alkyl-4-quinolone-(AQ)-dependent quorum sensing (QS) in *P. aeruginosa* was explored.

Figure 1:
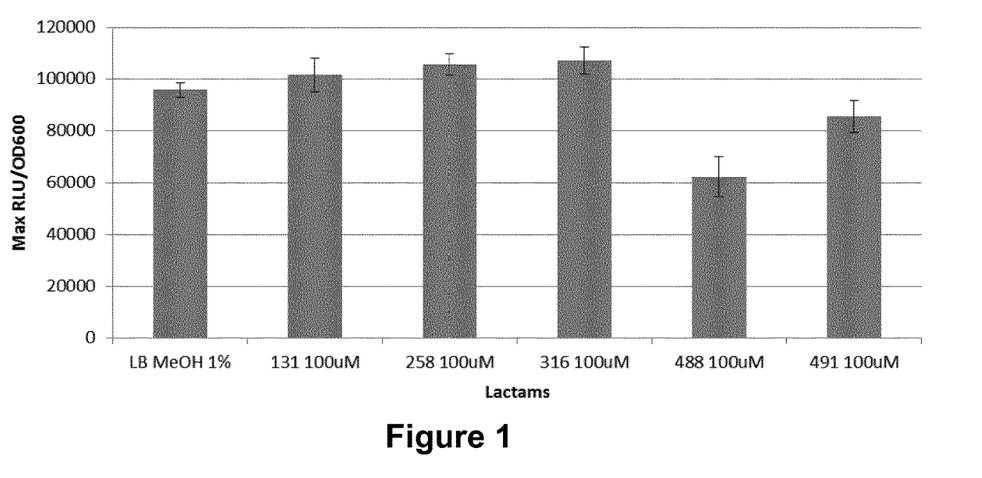
FIG. 1 shows a comparison of the expression of *P. aeruginosa* lasI::lux in the presence and absence of lactams 131, 258, 316, 488 and 491 at 100 µM. Control–LB medium+1% methanol.
Figure 2:
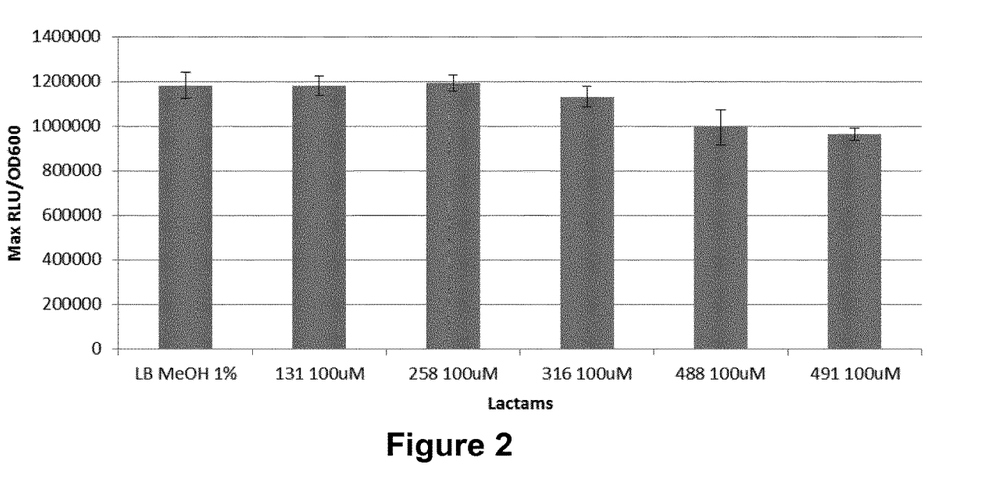
FIG. 2 shows a comparison of the expression of *P. aeruginosa* rhlI::lux in the presence and absence of lactams 131, 258, 316, 488 and 491 at 100 µM. Control–LB medium+1% methanol.

The expression of rhl and las AHL- and the pqsA AQ-synthase genes was evaluated using lux-based lasI (FIG. 1), rhlI (FIG. 2) and pqsA (FIG. 3) chromosomally integrated promoter fusions. Luminescence was quantified as a function of bacterial growth. The applicant further determined that none of the lactams is growth inhibitory at 100 µM using a large number of strains (figure not shown).

Figure 4:
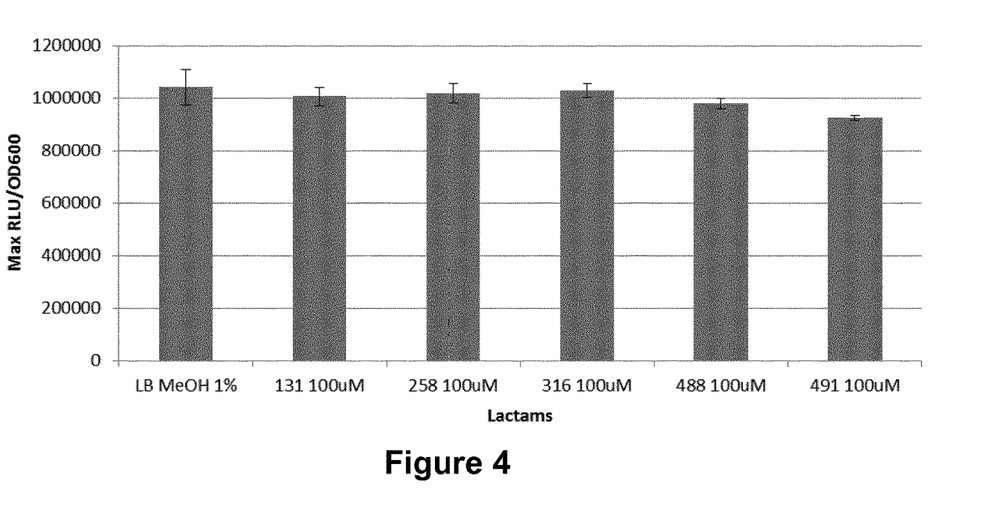
FIG. 4 shows a comparison of the expression of *P. aeruginosa* tac::lux in the presence and absence of Unilever lactams 131, 258, 316, 488 and 491 at 100 µM. Control–LB medium+1% methanol.

The *P. aeruginosa* PAO1-N tac::lux strain was used as a positive control biosensor as it constitutively expresses luxCDABE and hence light (FIG. 4). Any reduction in light output in this strain in the presence of a lactam will show whether or not the compound has an adverse effect on luminescence per se. The tac::lux expression profile shows that there is no interference between the compounds and the enzymes involved in light generation. Any effects observed on incubation of the QS reporter strains with the lactams will therefore be due to alterations in promoter expression.

The qualitative effect of compound 4-(4-chlorophenyl)-5-methylene-pyrrol-2-one (Ref. 488) on pyocyanin production by PAO1-L was then investigated.

Figure 3:
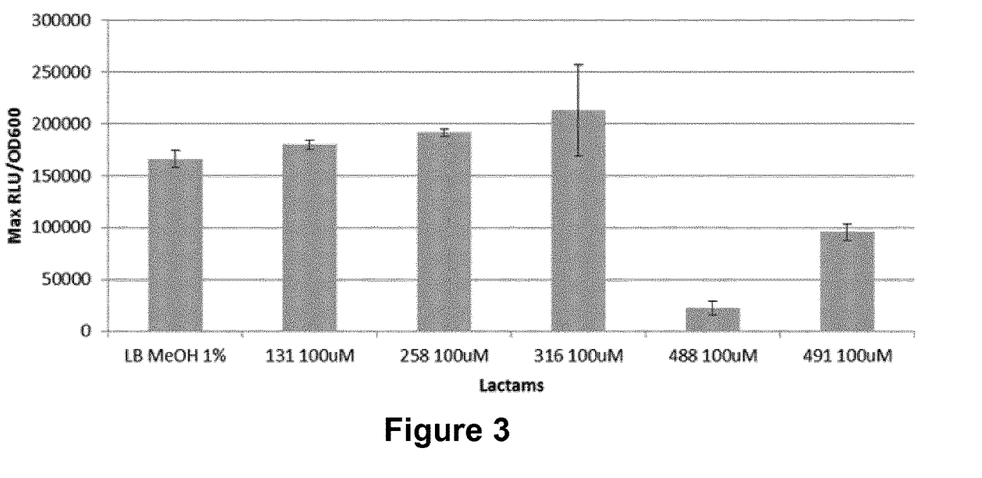
FIG. 3 shows a comparison of the expression of *P. aeruginosa* pqsA::lux in the presence and absence of Unilever lactams 131, 258, 316, 488 and 491 at 100 µM. Control–LB medium+1% methanol.

Pyocyanin is a blue redox-active secondary metabolite and a putative signalling molecule in *P. aeruginosa* (Jayaseelan et al, 2014). The pyocyanin biosynthetic (phz) genes are regulated by QS and in part via the transcriptional regulator PqsR acting through PqsE (Rampioni et al 2011). Pyocyanin production was visually assessed after 8 h of incubation at 37° C. in *P. aeruginosa* strain PAO1-L in the presence and absence of compound 4-(4-chlorophenyl)-5-methylene-pyrrol-2-one (Ref. 488), which FIG. 3 shows was the most potent inhibitor of the PqsR-dependent pqsA::lux promoter fusion.

Figure 5:
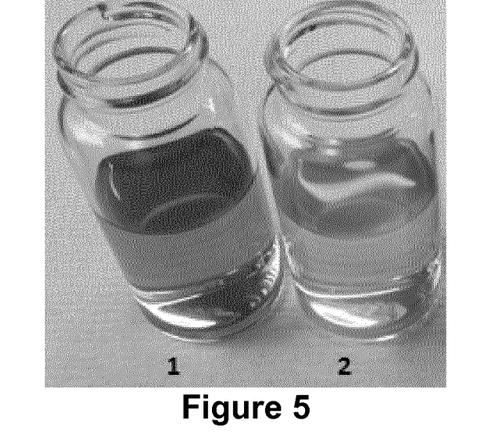
FIG. 5 shows vials demonstrating pyocyanin production by PAO1-L grown in the presence of lactam 488 in 0 (1), 100 (2) and 10 µM (3). (4) is an LB only control.

FIG. 5 shows the culture supernatants of PAO1-L grown in the absence or presence of lactam 4-(4-chlorophenyl)-5-methylene-pyrrol-2-one (Ref. 488).

The inhibition of pyocyanin production by lactam 4-(4-chlorophenyl)-5-methylene-pyrrol-2-one (Ref. 488) was observed as the absence of green pigmentation in culture supernatant in vial 2 (FIG. 5). Although qualitative, this observation offers further confirmation of the inhibitory effects of lactam 4-(4-chlorophenyl)-5-methylene-pyrrol-2-one (Ref. 488) on AQ-dependent QS.

The inhibitory properties of compounds of the invention on AQ-dependent QS in *P. aeruginosa* were then investigated.

In *P. aeruginosa*, the pqsABCDE genes code for the biosynthetic pathway required for the synthesis and action of 2-alkyl-4(1H)-quinolones (AQs) (Heeb et al 2010). The transcriptional activator PqsR regulates the expression of the pqs biosynthetic pathway that in turn controls secondary metabolites such as elastase, pyocyanin and phospholipase as well as biofilm maturation and swarming motility. In this QS system, the primary AQ signal molecules are 4-hydroxy-2-heptylquinoline (HHQ) and 2-heptyl-3-hydroxy-4-quinolone (PQS) both of which act as co-inducers of PqsR (Heeb et al 2010; Ilangovan et al 2013).

The results from the first screening experiments (FIG. 1-3) using AHL and AQ biosensor strains clearly show that inhibition of the pqs-system is the main effect of lactams 4-(4-chlorophenyl)-5-methylene-pyrrol-2-one (Ref. 488) and 5-methylene-4-(p-tolyl)pyrrol-2-one (Ref. 491) on QS in *P. aeruginosa*. To determine the relative inhibitory activities ($IC_{50s}$) of 4-(4-chlorophenyl)-5-methylene-pyrrol-2-one (Ref. 488) and 5-methylene-4-(p-tolyl)pyrrol-2-one (Ref. 491), dose response curves were constructed using the same biosensor strain (*P. aeruginosa* PAO1 pqsA::lux; Fletcher et al, 2007; Ilangovan et al 2013). This strain produces light in response to the endogenous production of AQs such as PQS and HHQ. The data obtained are presented in FIG. 6 and FIG. 7 from which $IC_{50s}$ were calculated as 22 µM for 4-(4-chlorophenyl)-5-methylene-pyrrol-2-one (Ref. 488) and 44 µM for 5-methylene-4-(p-tolyl)pyrrol-2-one (Ref. 491) respectively. While 4-(4-chlorophenyl)-5-methylene-pyrrol-2-one (Ref. 488) is the more potent of the two compounds, 5-methylene-4-(p-tolyl)pyrrol-2-one (Ref. 491) showed the desired effect. It can also be seen that 5-methylene-4-(p-tolyl)pyrrol-2-one (Ref. 491) did not inhibit pqsA expression as strongly as 4-(4-chlorophenyl)-5-methylene-pyrrol-2-one (Ref. 488) at high concentrations while 4-(4-chlorophenyl)-5-methylene-pyrrol-2-one (Ref. 488) completely inhibited light output and hence pqsA expression.

Figure 6:
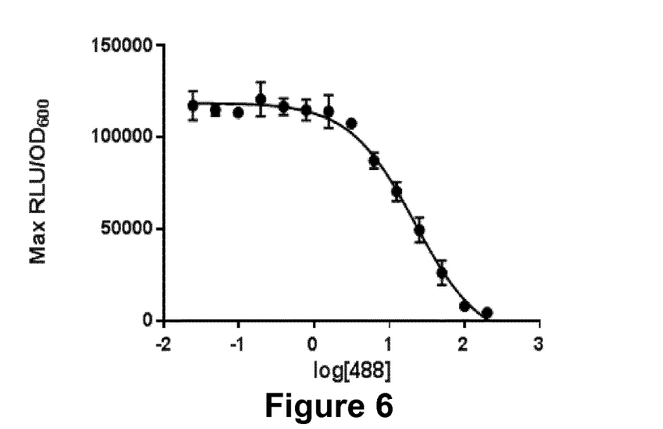
FIG. 6 shows the effect of lactam 488 on the expression of pqsA::lux in *P. aeruginosa* PAO1-L.
Figure 7:
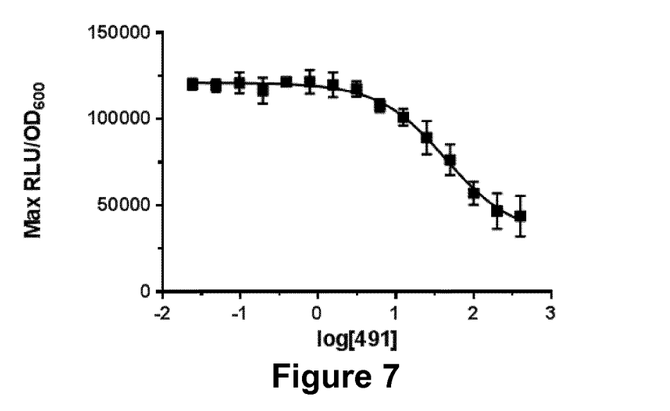
FIG. 7 shows the effect of lactam 491 on expression of pqsA::lux in *P. aeruginosa* PAO1-L.

FIGS. 6 and 7 demonstrate the binding and inhibition of the PQS quorum sensing in *pseudomonas*, with compound 488 showing the ability to fully knock out the PQS. The 491 compound in FIG. 7 whist proving inhibition did not give complete knock out at higher concentration.

The mode of action on AQ-dependent QS was investigated.

The major QS molecules in the pqs system are the AQs, PQS and its precursor HHQ (Williams & Camara 2009). Their biosynthesis requires the regulator PqsR and the biosynthetic proteins, PqsABCD and the mono-oxygenase, PqsH (Heeb et al 2010).

The inhibitory action of 4-(4-chlorophenyl)-5-methylene-pyrrol-2-one (Ref. 488) may involve inhibition of AQ biosynthesis or 4-(4-chlorophenyl)-5-methylene-pyrrol-2-one (Ref. 488) may behave like an antagonist and block the PQS receptor, PqsR. These experiments do not discriminate between inhibition of PqsR activation and inhibition of AQ biosynthesis because the biosensor strain used maintains an intact AQ-dependent QS system. Experiments were therefore designed to determine the nature and degree of 4-(4-chlorophenyl)-5-methylene-pyrrol-2-one (Ref. 488) inhibitory activity. Firstly, the possibility that 4-(4-chlorophenyl)-5-methylene-pyrrol-2-one (Ref. 488) is an inhibitor of the response regulator protein, PqsR that is essential for expression of the pqsABCDE genes and hence AQ production was explored.

Figure 8:
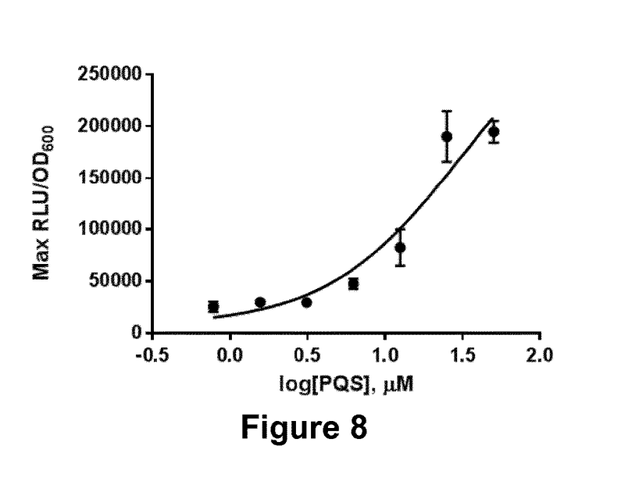
FIG. 8 shows the effect of PQS on the expression of pqsA::lux in PAO1-L ΔpqsA in presence of lactam 488 $EC_{50}$ for PQS increased from 2 µM to 31 µM in the presence of 488 (215 µM).

By using the AQ-non producing *P. aeruginosa* strain PAO1-L ΔpqsA, pqsA::lux, the $EC_{50}$ value for the native PqsR agonist, PQS was calculated as ~2 µM (Ilangovan et al. 2013). In the presence of a fixed concentration of lactam 4-(4-chlorophenyl)-5-methylene-pyrrol-2-one (Ref. 488) and a range of PQS concentrations, the $EC_{50}$ value increased ~15 fold to 31 µM (FIG. 8). This suggests that 4-(4-chlorophenyl)-5-methylene-pyrrol-2-one (Ref. 488) acts as a competitive antagonist of AQ signalling potentially inhibiting the interaction between PqsR and its co-inducer, PQS.

Figure 9:
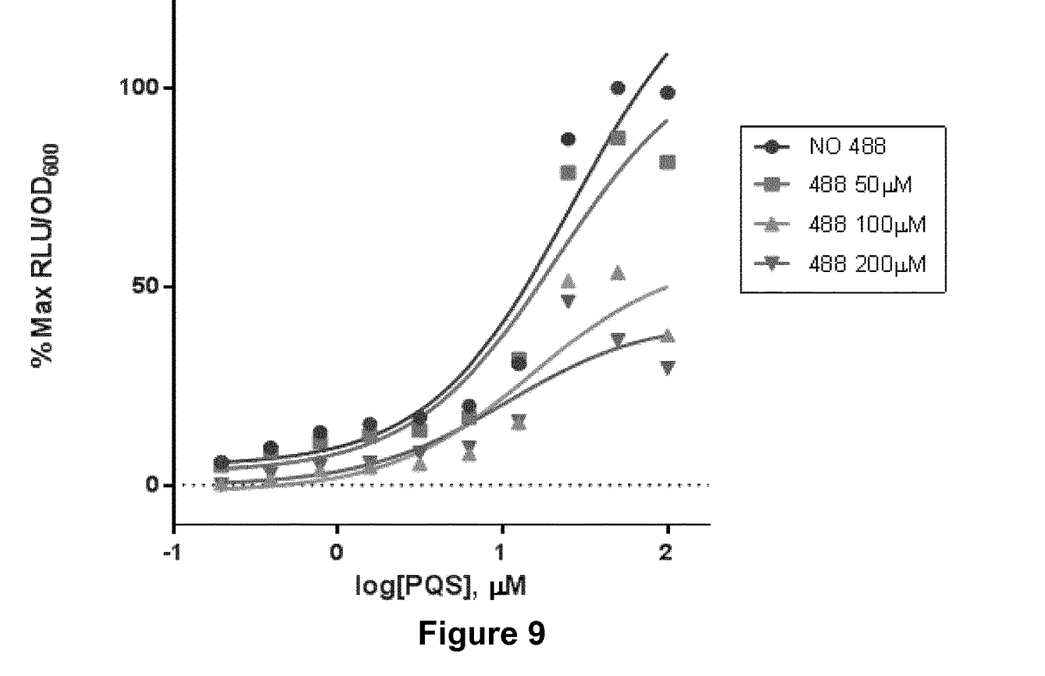
FIG. 9 shows the effect of 488 at 0, 50, 100, 200 µM on the PQS-dependent expression of pqsA'::lux in *P. aeruginosa* PAO1-L ΔpqsA. The data show that PQS competes with 488 for PqsR-dependent activation of pqsA'::lux fully restoring light output in the presence of 50 µM but not 100 µM or 200 µM of 488.

The experiment shown in FIG. 8 was then repeated using 4-(4-chlorophenyl)-5-methylene-pyrrol-2-one (Ref. 488) concentrations of 0, 50, 100 and 200 µM. The results obtained are shown in FIG. 9 which shows that as 4-(4-chlorophenyl)-5-methylene-pyrrol-2-one (Ref. 488) concentrations are increased, maximal light output is substantially reduced. The shape of the dose response curves indicates that 4-(4-chlorophenyl)-5-methylene-pyrrol-2-one (Ref. 488) is a competitive antagonist as increasing the PQS concentration, restores pqsA::lux expression.

These data demonstrate the selective binding and competitive antagonist activity of 4-(4-chlorophenyl)-5-methylene-pyrrol-2-one (Ref. 488).

Figure 10:
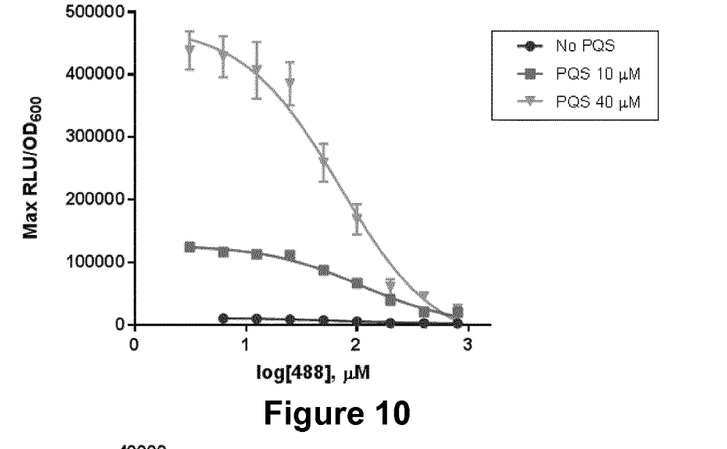
FIG. 10 shows the effect lactam 488 on the expression of pqsA'::lux in PAO1ΔpqsA in the presence of PQS at 0 µM, 10 µM or 40 µM.

A PAO1-L ΔpqsA pqsA'::lux biosensor-based assay was performed to determine whether lactam 4-(4-chlorophenyl)-5-methylene-pyrrol-2-one (Ref. 488) exhibits any partial agonist activity at higher concentrations. A partial agonist is a molecule that can bind to and activate a receptor resulting in a non-complete response compared with a full agonist. Graphically, an antagonist that is also a partial agonist exhibits agonist activity at high concentrations. FIG. 10 shows that 4-(4-chlorophenyl)-5-methylene-pyrrol-2-one (Ref. 488) has no partial agonist activity as it was unable to activate pqsA expression at concentrations up to 800 µM. This contrasts with its activity as an antagonist in the presence of 10 or 40 µM PQS. This demonstrates that at higher concentrations there is no activation of receptor binding, offering low or even no toxicity at higher doses.

Figure 11:
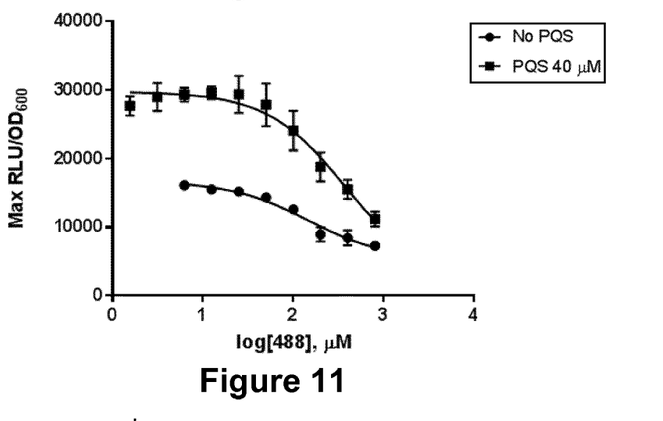
FIG. 11 shows the PqsR-independent activity of 488 on the expression of pqsA'::lux in PAO1-N ΔpqsAHR.

PQS is capable of weakly activating pqsA in the absence of PqsR via a mechanism that is not fully understood but appears to depend on the iron chelating properties of PQS. The aim of this experiment was to clarify whether lactam 4-(4-chlorophenyl)-5-methylene-pyrrol-2-one (Ref. 488) is also inhibitory for pqsA expression via the PqsR independent pathway. As previously described, the pqsA'::lux biosensor based on the triple mutant PAO1-N ΔpqsAHR cannot produce AQs and lacks pqsR but still responds to exogenous PQS. This response is however much weaker that the PqsR-dependent response. FIG. 11 shows the impact of 4-(4-chlorophenyl)-5-methylene-pyrrol-2-one (Ref. 488) on the PqsR-independent expression of pqsA in the presence or absence of 40 µM PQS. 4-(4-chlorophenyl)-5-methylene-pyrrol-2-one (Ref. 488) has a small inhibitory effect on the PqsR-independent pathway. This suggests that while the compounds of the invention may have some effect on *P.* aeruginosa that do not express AQs, they show most promise for in the treatment of disorders in which AQ-producing strains are implicated.

Indeed for 4-(4-chlorophenyl)-5-methylene-pyrrol-2-one (Ref. 488) the PQS pathway is the dominant inhibitory route. Taking into account the role of quorum sensing in toxicity and virulence of pseudomonas, then this technology is most effective against those strains capable of quorum sensing.

Figure 12:
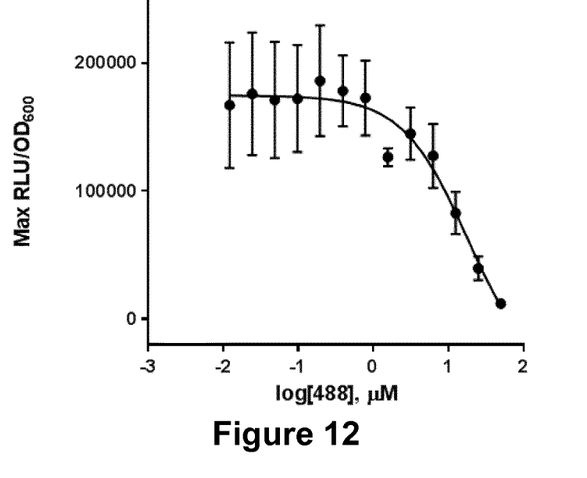
FIG. 12 shows the inhibitory effect of 488 on the expression of pqsA'::lux in *P. aeruginosa*.

To investigate the inhibitory effect of 4-(4-chlorophenyl)-5-methylene-pyrrol-2-one (Ref. 488) on *P. aeruginosa* PA14, a pqsA'::lux fusion was introduced onto the chromosome. Comparable inhibitory effects with those previously described for strain PAO1 were observed. The $IC_{50}$ extrapolated from the inhibition curve in FIG. 12 was calculated to be 17.9 µM.

To determine whether 4-(4-chlorophenyl)-5-methylene-pyrrol-2-one (Ref. 488) is capable of inhibiting the enzymes (PqsABCD) involved in AQ biosynthesis, the *P. aeruginosa* PAO1-N ΔpqsAHR was exploited. This mutant cannot produce AQs because the genes coding for the key biosynthetic enzymes (PqsA and PqsH) and regulation (PqsR) have been deleted. To restore AQ production in a PqsR-independent manner in PAO1-N ΔpqsA, the pqsABCD genes were introduced on a plasmid (pBBR pqsABCD; Niewerth et al. 2011). *P. aeruginosa* PAO1-N ΔpqsAHR and *P. aeruginosa* PAO1-N ΔpqsAHR pBBR pqsABCD were both incubated overnight in LB with and without 4-(4-chlorophenyl)-5-methylene-pyrrol-2-one (Ref. 488) (200 µM), resuspended to an $OD_{600}$ 1.0. The cultures were extracted with acidified ethyl acetate, the organic phase removed, dried and resuspended in methanol subjected to thin layer chromatography (TLC).

TABLE 1

| | |
|---|---|
| 1 | PQS, 10 mM + HHQ, 10 mM, 2 µl |
| 2 | 488 10 mM, 5 µl |
| 3 | PAO1-N ΔpqsAHR organic extract, 10 µl |
| 4 | PAO1-N ΔpqsAHR + 488 200 µM organic extract, 10 µl |
| 5 | PAO1-N ΔpqsAHR pBBR-pqsABCD organic extract, 10 µl |
| 6 | PAO1-N ΔpqsAHR pBBR-pqsABCD + 488 200 µM organic extract, 10 µl |

Figure 13:
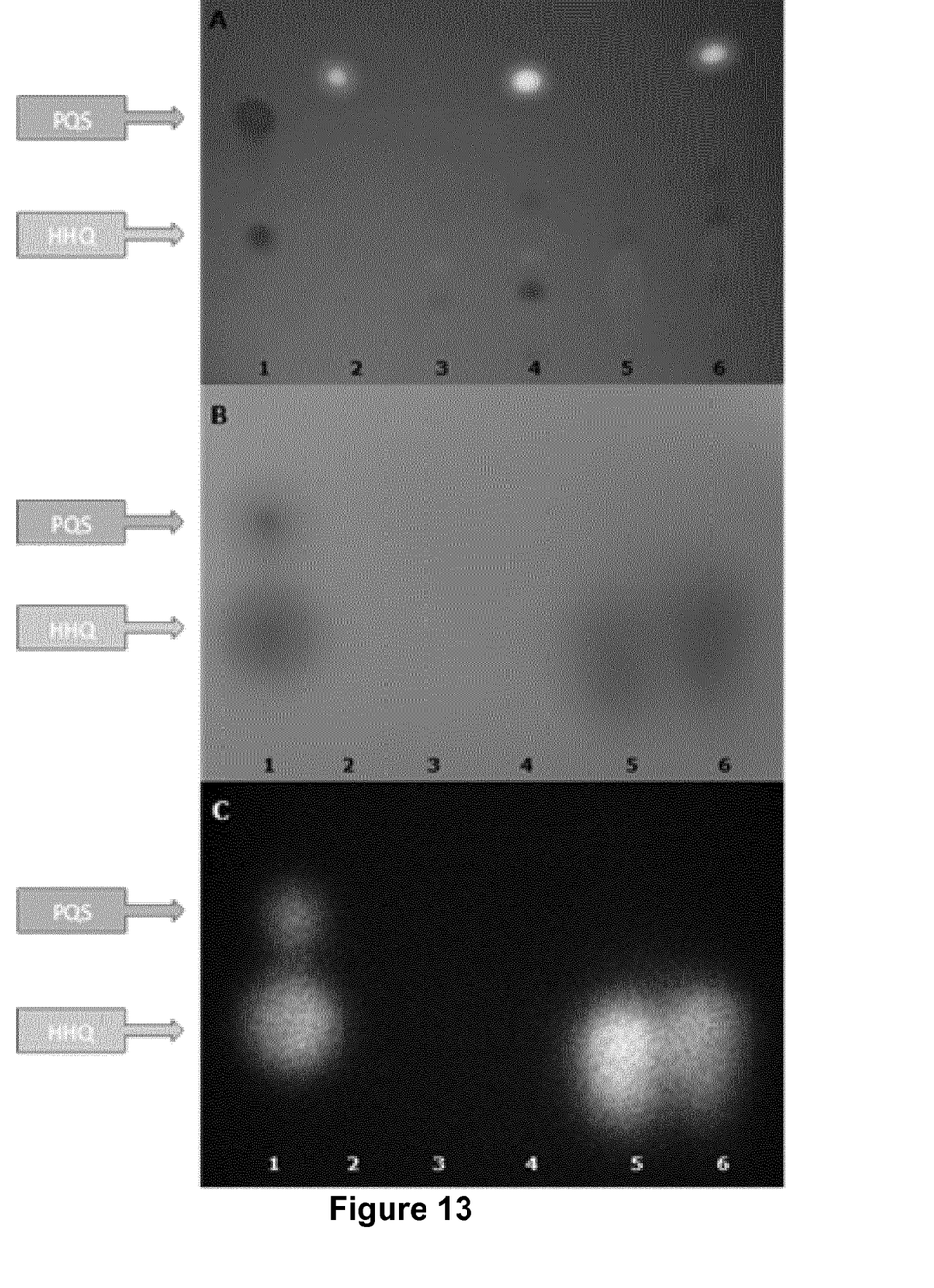
FIG. 13 shows TLC analysis of HHQ production. (Panel A) TLC plate under UV light at 312 nm, showing PQS (lane 1 upper spot) and HHQ (lane 1 lower spot) standards together, 488 standard (lane 2), organic solvent supernatant extracts of PAO1-N ΔpqsAHR grown without (lane 3) and with (lane 4) the compound 488 and organic solvent supernatant extracts of PAO1-N ΔpqsAHR pqsABCD grown without (lane 5) and with 488 (lane 6). Pyocyanin production (Panel B) and light output (Panel C) occurs via PAO1-L ΔpqsA CTX::pqsA'-luxCDABE present in the agar overlay. Both pyocyanin and light output are dependent on the presence of AQs. Bioluminescence was captured using a luminograph photon camera. The uppermost bright spot on the UV illuminated plate (Panel A, lanes 2, 4 and 6) is 488.

After chromatography using a dichloromethane-methanol mobile phase, the TLC plates were overlaid with a thin agar layer containing the AQ biosensor strain PAO1-L ΔpqsA CTX::pqsA'-luxCDABE (Fletcher et al. 2007) incubated and examined for reporter output (FIG. 13). FIG. 13 panel A shows the TLC plate under UV illumination after chromatography. The biosensor strain produces light (FIG. 13 panel C) and pyocyanin (FIG. 13 panel B) in response to AQs that bind to PqsR and activate the pqsA promoter.

The biosensor revealed the presence of HHQ both in the samples of PAO1-N ΔpqsAHR pBBR-pqsABCD without (FIG. 13 panels B and C; lane 5) and with (FIG. 13 panels B and C lane 6) compound 4-(4-chlorophenyl)-5-methylene-pyrrol-2-one (Ref. 488) indicating that the lactam did not inhibit HHQ biosynthesis.

Sources of Bacterial Strains

The bacterial strains were obtained or made as follows:

TABLE 2

| Strain | Antibiotic | Source or reference |
|---|---|---|
| *Escherichia Coli:* | | |
| S17-1 pMiniCTX-pqsA::lux | Gentamycin 25 µg/ml | Diggle et al., 2007 |

TABLE 2-continued

| Strain | Antibiotic | Source or reference |
|---|---|---|
| DH5 pBBRMCS-5::pqsABCD | Gentamycin 25 µg/ml | Niewerth et al., 2011 |
| *Pseudomonas aeruginosa:* | | |
| PAO1-L | — | Halloway collection |
| PAO1-N | — | Halloway collection |
| PAO1-L ΔpqsA | — | This study |
| PAO1-L ΔpqsA, pqsA::lux | Gentamycin 25 µg/ml | This study |
| PAO1-N ΔpqsA | — | Aendekerk et al., 2005 |
| PAO1-N ΔpqsA, pqsA::lux | Tetracyclin 125 µg/ml | Diggle et al., 2007 |
| PAO1-N ΔpqsAH | — | Diggle et al., 2007 |
| PAO1-N ΔpqsAH, pqsA::lux | Gentamycin 25 µg/ml | Diggle et al., 2007 |
| PAO1-N ΔpqsAHR | — | Ilangovan at al., 2013 |
| PAO1-N ΔpqsAHR, pqsA::lux | Gentamycin 25 µg/ml | By applicant |
| PAO1-L ΔpqsAHR, pqsABCD | Gentamycin 25 µg/ml | By applicant |
| PAO1-L ΔrhlI | — | Dr. Matthew Fletcher |
| PAO1-L ΔlasI | — | Dr. Matthew Fletcher |
| PAO1-L pqsA::lux | Gentamycin 25 µg/ml | By applicant |
| PAO1-L las::lux | Gentamycin 25 µg/ml | James Lazenby. Unpublished' |
| PAO1-L rhlI::lux | Gentamycin 25 µg/ml | James Lazenby. Unpublished' |
| PAO1-N tac::lux | Tetracyclin 125 µg/ml | By applicant |
| PA ATCC 15442 | — | Unilever* |
| PA ATCC 15442, pqsA::lux | Gentamycin 25 µg/ml | By applicant |
| PA14 | | Rahme et al., 1995 |
| PA14, pqsA::lux | Gentamycin 25 µg/ml | By applicant |

*accession no. AYUC00000000 on DDBJ/EMBL/GenBank

Summary of Biological Activity

The examples demonstrate that compounds of the invention have been shown to:
- inhibit alkylquinolone (AQ) dependent quorum sensing (QS) in *P. aeruginosa*.
- inhibit PqsR in representative strains belonging to the major *P. aeruginosa* genomic groups (PAO1 and PA14 respectively).
- interact antagonistically with the LysR-type regulator PqsR (in a competitive manner without partial-agonist activity).
- do not appear to directly inhibit AQ biosynthesis but block AQ synthesis by acting as a PqsR antagonist.
- potentially interact with the co-inducer binding domain of PqsR ($PqsR^{CBD}$) acting an allosteric inhibitors.

This provides an unusual biological profile that may enable compounds of the invention to be useful in the treatment of chronic respiratory tract disorders stemming from bacterial infection. In particular, the biological profile of the compounds of the invention offer utility in the treatment of chronic respiratory tract disorders experienced by cystic fibrosis patients. This is because the compounds of the invention have a biological activity profile that controls multiplication and biofilm formation, but does not trigger the bio-pathways that are associated with developing antibacterial resistance.

REFERENCES

The references cited herein are incorporated by reference in their entirety for all purposes:

Aendekerk S, Diggle S P, Song Z, Høiby N, Cornelis P, Williams P, Cámara M. The MexGHI-OpmD multidrug efflux pump controls growth, antibiotic susceptibility and virulence in *Pseudomonas aeruginosa* via 4-quinolone-dependent cell-to-cell communication. (2005) *Microbiology* 151(4) 1113-25.

Barr H L, Halliday N, Cámara M, Barrett D A, Williams P, Forrester D L, Simms R, Smyth A R, Honeybourne D, Whitehouse J L, Nash E F, Dewar J, Clayton A, Knox A J, Fogarty A W. (2015) *Pseudomonas aeruginosa* quorum sensing molecules correlate with clinical status in cystic fibrosis. *European Respiratory Journal* 46 (4) 1046-1054.

Fletcher M P, Diggle S P, Cámara M & Williams, P. (2007) Biosensor-based assays for PQS, HHQ and related 2-alkyl-4-quinolone quorum sensing signal molecules. *Nature Protocols*, 2, 1254-1262 doi:10.1038/nprot.2007.158.

Fletcher M P, Diggle S P, Cámara M. and Williams P. (2007) Biosensor-based assays for PQS, HHQ and related 2-alkyl-4-quinolone quorum sensing signal molecules. *Nature protocols*, 2, 1254-62.

Freschi et al. (2015) Clinical utilization of genomics data produced by the international *Pseudomonas aeruginosa* consortium. *Frontiers in microbiology* 6, Article 1036.

Ilangovan A, Fletcher M, Ramioni G, Pustelny C, Rumbaugh K, Heeb S, Cámara M, Truman A, Chhabra S R, Emsley J & Williams P. (2013) Structural basis for native agonist and synthetic inhibitor recognition by the *Pseudomonas aeruginosa* quorum sensing regulator PqsR (MvfR). PLOS Pathogens 9(7):e1003508.

Niewerth H, Bergander K, Chhabra S, Williams P, and Fetzner S. (2011) Synthesis and biotransformation of 2-alkyl-4(1H)-quinolones by recombinant *Pseudomonas putida* KT2440, *Applied Microbiology and Biotechnology*, 91, 1399-1408.

Rahme L G, Stevens E J, Wolfort S F, Shao J, Tompkins R G, et al. (1995) Common virulence factors for bacterial pathogenicity in plants and animals. *Science,* 268: 1899-1902.

The invention claimed is:

1. A method of treatment of cystic fibrosis in a subject comprising:
    administering to the subject an effective amount of a lactam of 4-(4-chlorophenyl)-5-methylene-pyrrol-2-one.

* * * * *